(12) United States Patent
Kosaku

(10) Patent No.: US 8,608,662 B2
(45) Date of Patent: Dec. 17, 2013

(54) ULTRASOUND DIAGNOSIS APPARATUS

(75) Inventor: Hideki Kosaku, Nasushiobara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 410 days.

(21) Appl. No.: 12/787,707

(22) Filed: May 26, 2010

(65) Prior Publication Data

US 2010/0305450 A1 Dec. 2, 2010

(30) Foreign Application Priority Data

Jun. 1, 2009 (JP) ................................. 2009-132460

(51) Int. Cl.
*A61B 8/14* (2006.01)

(52) U.S. Cl.
USPC ............................ 600/459; 600/407; 600/437

(58) Field of Classification Search
USPC ......... 600/407, 411, 437, 443, 444, 447, 449, 600/459, 461
See application file for complete search history.

(56) References Cited

U.S. PATENT DOCUMENTS

| | | | |
|---|---|---|---|
| 5,483,965 A * | 1/1996 | Wiener et al. | 600/449 |
| 2006/0103506 A1 * | 5/2006 | Rodgers et al. | 340/10.5 |
| 2007/0239006 A1 * | 10/2007 | Kamiyama et al. | 600/437 |
| 2009/0069690 A1 * | 3/2009 | Shin et al. | 600/459 |

FOREIGN PATENT DOCUMENTS

| | | |
|---|---|---|
| JP | 4-99909 U | 8/1992 |
| JP | 5-76528 A | 3/1993 |
| JP | 5-285136 A | 11/1993 |
| JP | 2003-70788 A | 3/2003 |
| JP | 2007-236823 A | 9/2007 |
| KR | 20090037666 A | 4/2009 |

OTHER PUBLICATIONS

KR Office Action for corresponding KR Application No. 10-2010-0045994 mailed on Jul. 1, 2011 with English Summary.
Japanese Office Action with English translation for Japanese patent Application No. 2009-132460 mailed on Aug. 13, 2013.

* cited by examiner

*Primary Examiner* — James Kish
*Assistant Examiner* — Michael N Fisher
(74) *Attorney, Agent, or Firm* — Yoshida & Associates, LLC

(57) ABSTRACT

An apparatus has: an ultrasound probe that transmits and receives ultrasound waves to and from a subject and has an ultrasound transmission/reception surface; an acoustic coupler that has a different shape for each type and is attachable and detachable so as to cover the ultrasound transmission/reception surface; a generator that, based on the ultrasound waves received by the ultrasound probe, generates an image expanding in a depth direction from the ultrasound transmission/reception surface; and an analyzer that, based on presence/absence and shape of an acoustic coupler region within the image generated by the generator, identifies presence/absence of mounting of the acoustic coupler and a type of the mounted acoustic coupler. Consequently, the apparatus is capable of identifying the acoustic coupler though the ultrasound probe and the acoustic coupler are not provided with special structures.

4 Claims, 7 Drawing Sheets

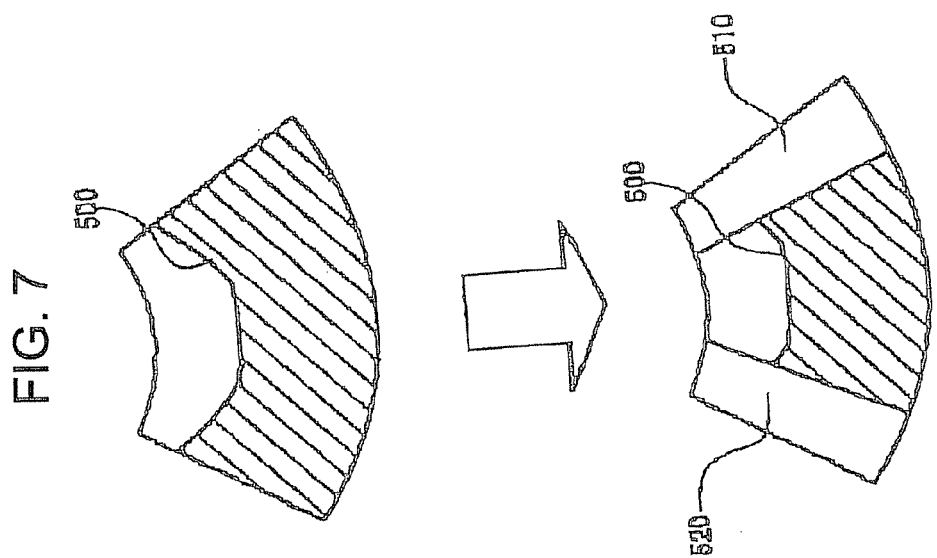

ULTRASOUND DIAGNOSIS APPARATUS

BACKGROUND OF THE INVENTION

1. Field of the Invention

The present invention relates to an ultrasound diagnosis apparatus. To be specific, the present invention relates to an ultrasound diagnosis apparatus provided with an ultrasound probe to and from which an acoustic coupler can be attached and detached.

2. Description of the Related Art

An ultrasound diagnosis apparatus is used for diagnosis of a heart and an abdominal organ like a liver, and is also used for diagnosis of other various sites. Conventionally, there is a case of mounting an acoustic coupler on the ultrasound transmission/reception surface of an ultrasound probe in order to appropriately regulate the ultrasound transmission/reception surface of the ultrasound probe and regulate the convergence speed of ultrasound waves for each site.

Therefore, the shape and material of the ultrasound transmission/reception surface of the acoustic coupler varies depending on a diagnosed site. In a state that an acoustic coupler having an ultrasound transmission/reception surface of appropriate shape and so on for each diagnosed site is selected and mounted on the ultrasound probe, diagnosis by the ultrasound diagnosis apparatus is performed.

When the acoustic coupler is mounted, the ultrasound diagnosis apparatus needs correction of a medical image, because mounting the acoustic coupler causes change in display depth on the medical image, refraction of an ultrasound beam, and so on. Also, the ultrasound diagnosis apparatus needs correction of a medical image, depending on the ultrasound propagation property of a diagnosed site. That is to say, when the acoustic coupler is mounted, the ultrasound diagnosis apparatus needs change of the conditions for transmission/reception of ultrasound waves in accordance with the type of the acoustic coupler.

Such change of the conditions for transmission/reception of ultrasound waves may require a complicated operation. Therefore, conventionally, a circuit such as a memory that stores identifications is installed in the acoustic coupler, and a circuit for acquiring the identification from the memory is installed in the ultrasound probe.

There is a proposal of a method of specifying the type of the mounted acoustic coupler based on the acquisition of the identification and correcting the thickness and sound speed value of the acoustic coupler (for example, refer to Japanese Unexamined Patent Application Publications Nos. 5-76528 and 2003-70788).

However, such a method of storing identifications in an acoustic coupler and electrically reading the identifications has a problem that the structure of the acoustic coupler is complicated. Moreover, there is a problem that the ultrasound probe needs a structure for recognizing the identification and therefore the structure of the ultrasound probe is complicated.

SUMMARY OF THE INVENTION

The present invention was made in consideration of the aforementioned problems. An object of the present invention is to provide an ultrasound diagnosis apparatus capable of identifying an acoustic coupler, without installing electrically special structures for identifying the type of the acoustic coupler into the acoustic coupler and an ultrasound probe.

In order to solve the abovementioned problems, in an aspect of the present invention, an ultrasound diagnosis apparatus has: an ultrasound probe configured to transmit and receive ultrasound waves to and from a subject and provided with an ultrasound transmission/reception surface; an acoustic coupler whose shape varies with the type, configured to be attachable and detachable so as to cover the ultrasound transmission/reception surface; a generator configured to, based on the ultrasound waves received by the ultrasound probe, generate an image expanding in a depth direction from the ultrasound transmission/reception surface; and an analyzer configured to identify presence/absence of mounting of an acoustic coupler and a type of the mounted acoustic coupler, based on presence/absence and shape of an acoustic coupler region within the image generated by the generator.

The analyzer may be configured to previously store patterns representing various shapes of the acoustic coupler region within the image and identify presence/absence of mounting of the acoustic coupler and the type of the mounted acoustic coupler by matching the patterns with the image generated by the generator.

The ultrasound diagnosis apparatus may further have a controller configured to control ultrasound transmission/reception conditions of the ultrasound probe. The controller is configured to change the ultrasound transmission/reception conditions based on presence/absence of mounting of the acoustic coupler and the type of the mounted acoustic coupler identified by the analyzer.

The controller may be configured to, when the analyzer identifies mounting of the acoustic coupler having the ultrasound transmission/reception surface with a larger radius of curvature than a radius of curvature of the ultrasound transmission/reception surface of the ultrasound probe, control the ultrasound probe to change a range to scan with the ultrasound waves to a predetermined restricted range narrower than the ultrasound transmission/reception surface of the acoustic coupler.

The analyzer may be configured to perform the identification at predetermined time intervals.

According to the present invention, it is possible to identify an acoustic coupler without providing an ultrasound probe and the acoustic coupler with special structures.

BRIEF DESCRIPTION OF THE DRAWINGS

FIG. 7 is a schematic view showing an example of a medical image after control.

DETAILED DESCRIPTION OF THE EMBODIMENTS

An embodiment of an ultrasound diagnosis apparatus according to the present invention will be specifically described below with reference to the drawings.

Figure 1:
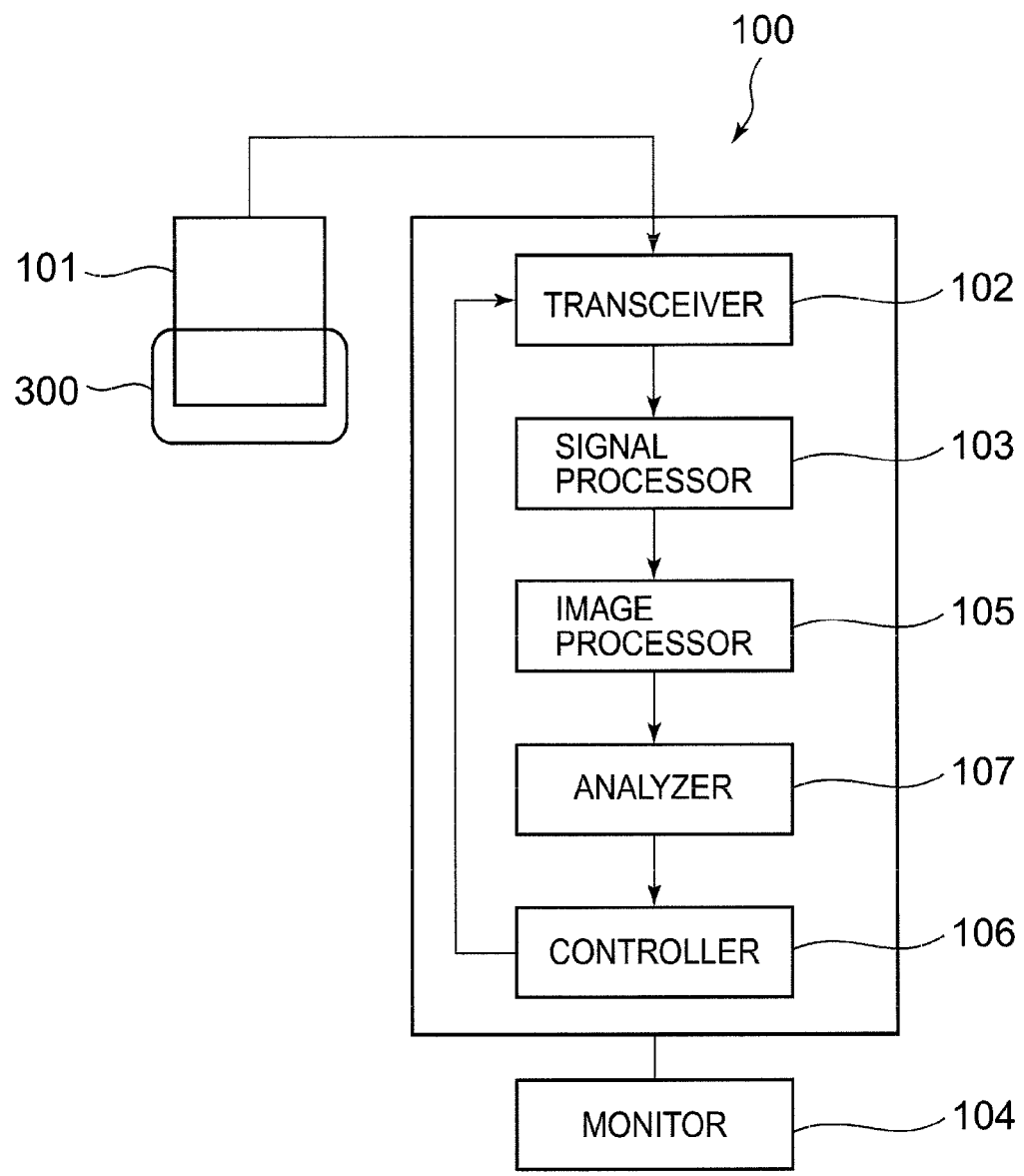
FIG. 1 is a block diagram showing an internal configuration of an ultrasound diagnosis apparatus according to the present invention.

An ultrasound diagnosis apparatus 100 shown in FIG. 1 transmits ultrasound waves to a subject. The ultrasound diagnosis apparatus 100 receives the ultrasound waves reflected from the subject, and generates and displays a medical image of the inside of the subject. The conditions for transmission/reception of ultrasound waves may vary depending on presence/absence of mounting of an acoustic coupler 300 and the type of the mounted acoustic coupler 300. Presence/absence of mounting of the acoustic coupler 300 and the type of the mounted acoustic coupler 300 are identified based on the analysis of a generated medical image. The conditions for transmitting and receiving ultrasound waves include control parameters such as a transmission voltage, a transmission waveform, a pulse repetition frequency, an ultrasound scan range, a focus, a gain and a speed of sound, for example.

The ultrasound diagnosis apparatus 100 has an ultrasound probe 101, a transceiver 102, a signal processor 103, and an image processor 105. The ultrasound probe 101 is connected to the transceiver 102. The transceiver 102 is connected to the signal processor 103. The signal processor 103 is connected to the image processor 105. The ultrasound diagnosis apparatus 100 generates a medical image of the inside of the subject based on transmission/reception of ultrasound waves. Besides, the ultrasound diagnosis apparatus 100 has a monitor 104, a controller 106, and an analyzer 107.

Figure 2:
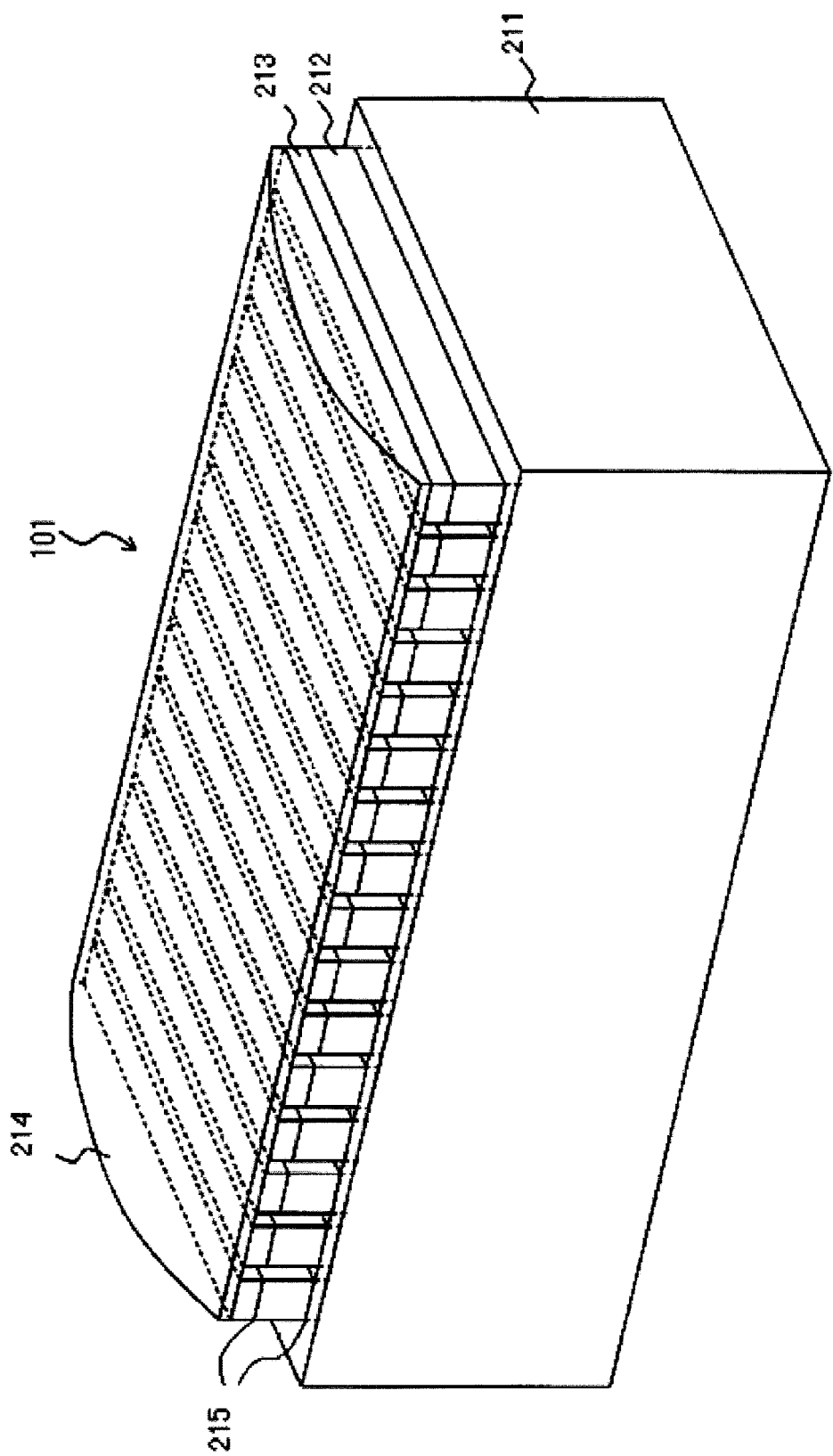
FIG. 2 is a schematic view showing an internal configuration of an ultrasound probe.

FIG. 2 is a schematic view showing an internal configuration of the ultrasound probe 101. The ultrasound probe 101 is connected to the ultrasound diagnosis apparatus 100 to transmit and receive ultrasound waves to and from the subject. The ultrasound probe 101 is configured by sequentially stacking ultrasound transducers 212, an acoustic matching layer 213 and an acoustic lens 214 on one surface of a backing material 211. The ultrasound transducers 212 are each held by an electrode pair 215. The backing material 211, the ultrasound transducers 212, the acoustic matching layer 213, the acoustic lens 214 and the electrode pairs 215 are contained in a probe case. A surface of the probe on the acoustic lens 214 side is an ultrasound transmission/reception surface, through which ultrasound waves are transmitted to the outside and received from the outside.

The ultrasound transducer 212 is an element having a piezoelectric effect, which enables reversible conversion between audio and electricity.

For the ultrasound transducers 212, piezoelectric ceramic elements such as lead zirconate titanate (Pb(Zr, Ti)O$_3$), lithium niobate (LiNbO$_3$), barium titanate (BaTiO$_3$) or lead titanate (PbTiO$_3$) are used.

The ultrasound transducers 212 are placed on a flat surface in a form such as a 1D array or a 2D array. The 1D array is a form of placing the strip-shaped ultrasound transducers 212 in the array direction. The 2D array is a form of placing the ultrasound transducers 212 like a matrix.

When a voltage is applied, the ultrasound transducers 212 transmit ultrasound waves in a direction of stacking the backing material 211 and the acoustic matching layer 213. On the other hand, when receiving the reflected waves from the inside of the subject, the ultrasound transducers 212 output electric signals.

The electrode pair 215 applies voltages to the ultrasound transducer 212 held thereby. The electric signals outputted when the ultrasound transducers 212 receive the reflected waves flow to the electrode pairs 215. The electrode pairs 215 are disposed so as to correspond to the respective ultrasound transducers 212. Signal electrodes for the respective ultrasound transducers 212 are connected to the surfaces of the ultrasound transducers 212 on the backing material 211 side. A common electrode (GND) is connected to the surfaces of the ultrasound transducers 212 on the acoustic matching layer 213 side.

The backing material 211 attenuates and absorbs unnecessary ultrasound vibration components for image generation of the ultrasound diagnosis apparatus, among the transmitted ultrasound waves and received reflected waves by the ultrasound transducers 212.

Moreover, the backing material 211 conveys heat generated in transmission of the ultrasound waves to a heat radiating member such as a cable part (not shown in the drawing). The backing member 211 is composed of a material with a large ultrasound attenuation rate or a material with a high thermal conductivity. For example, a generally used material is obtained by mixing inorganic particle powder of tungsten, ferrite, zinc oxide or the like into synthetic rubber, epoxy resin, urethane rubber or the like.

The acoustic matching layer 213 inhibits reflection of the ultrasound waves on the surface of the subject resulting from mismatching of acoustic impedance. The acoustic matching layer 213 has intermediate acoustic impedance between the acoustic impedance of the ultrasound transducers 212 and the acoustic impedance of the surface of the subject. For the acoustic matching layer 213, epoxy resin, plastic materials or the like is used. The acoustic matching layer 213 may be composed of a plurality of layers with different acoustic impedance in order to gradually make the acoustic impedance thereof closer to that of the surface of the subject.

The acoustic lens 214 comes in contact with the surface of the subject to mediate transmission/reception of the ultrasound waves. The acoustic lens 214 has a convex surface on the subject side. The acoustic lens 214 focuses the ultrasound waves oscillated by the ultrasound transducers 212, thereby making an acoustic focus at a predetermined depth of the subject.

Figure 3:
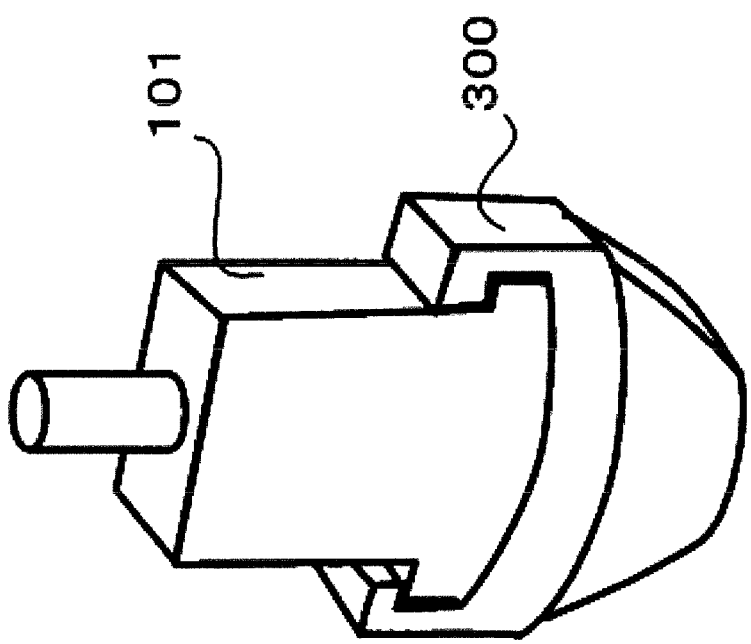
FIG. 3 is a schematic view showing an acoustic coupler.

As shown in FIG. 3, an acoustic coupler 300 is mounted on the ultrasound probe 101 so as to be removable therefrom. The sound pressure distribution in a region near the acoustic lens 214 is complicated and dynamic. Therefore, it is impossible to obtain a favorable image even if processing signals from this region. Thus, it is possible to obtain a favorable image by placing the acoustic coupler 300 so as to come in contact with the acoustic lens 214 and using a uniform sound field from the surface of a living body without using a sound field in the region near the lens.

The acoustic coupler 300 has a rear surface that has substantially the same shape as the ultrasound transmission/reception surface of the ultrasound probe 101. The acoustic coupler 300 is mounted with the rear surface in close contact with the ultrasound transmission/reception surface of the ultrasound probe 101. The acoustic coupler 300 has predetermined thickness in a direction of transmission/reception of the ultrasound waves when mounted on the ultrasound probe 101. The shape of a front surface, namely, the shape of the ultrasound transmission/reception surface of the acoustic coupler 300 varies depending on the type of the acoustic coupler 300. The acoustic coupler 300 has hooks upright from both the side surfaces over the rear surface, and is mounted with the hooks fitted with steps of the ultrasound probe 101. When the hooks are expanded to release the fitted state, the acoustic coupler 300 is removed from the ultrasound probe 101.

FIGS. 4A, 4B, 4C, 4D, 4E and 4F show medical images obtained with the acoustic couplers 300 of various types mounted, respectively.

These figures illustrate examples of the acoustic coupler 300.

The acoustic coupler 300 is shown in an upper region (referred to as a coupler region 301 hereinafter) of each of the medical images.

This coupler region 301 is distinguished from the other region, and has a pixel value representing the acoustic coupler 300. Use of a material with low thermal conductivity as the material for coupler makes the acoustic coupler 300 hard to convey heat resulting from a transmission output to a living body, and it becomes possible to increase the transmission output.

As the material for coupler, rubbers like butadiene rubber, resins, a mixture of butadiene rubber and silicone, a mixture of butadiene rubber and zinc oxide, and so on are preferably used. As the material for coupler, a material having acoustic impedance approximate to that of a human body and presenting small attenuation due to propagation of ultrasound waves is also preferably used. Besides, as the material for coupler, a material whose property is regulated by silicone, zinc oxide or the like of a mixture is also preferably used.

It is desirable that the degree of ultrasound attenuation of the material for coupler is 0.2 dB/mmMHz or less. Although it is possible to realize a material for coupler with the degree of attenuation of 0.05 dB/mmMHz or less by a certain mixture ratio, a difference in acoustic impedance between the coupler and a living body having acoustic impedance of 1.5 Mrayl is large. Consequently, reflection between the coupler and the acoustic lens or living body may become large. The acoustic couplers 300 of various types each have a composition in consideration of the acoustic impedance of a region of interest as a diagnosed site.

The acoustic coupler 300 has a pixel value that allows distinguishing from a living body based on a difference in attenuation rate. Since reflection of ultrasound waves within the acoustic coupler 300 is small in general, the pixel value of the coupler region 301 is low on a medical image. Therefore, the coupler region 301 is distinguished from other regions, and has a pixel value representing the acoustic coupler 300.

Figure 4A:
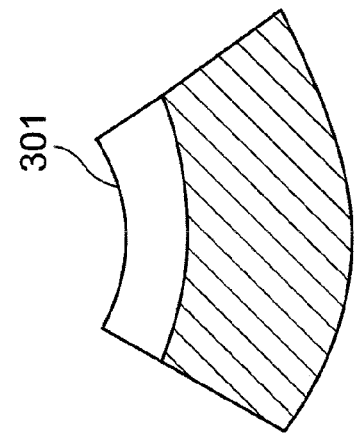
FIG. 4A is a schematic view showing a medical image when an acoustic coupler is mounted.
Figure 4B:
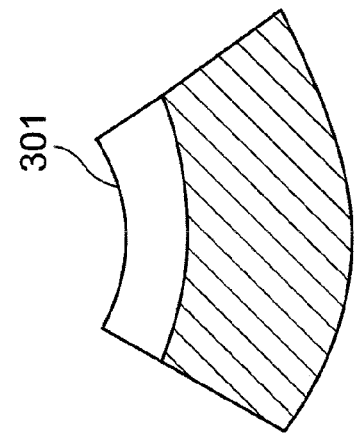
FIG. 4B is a schematic view showing a medical image when an acoustic coupler is mounted.
Figure 4C:
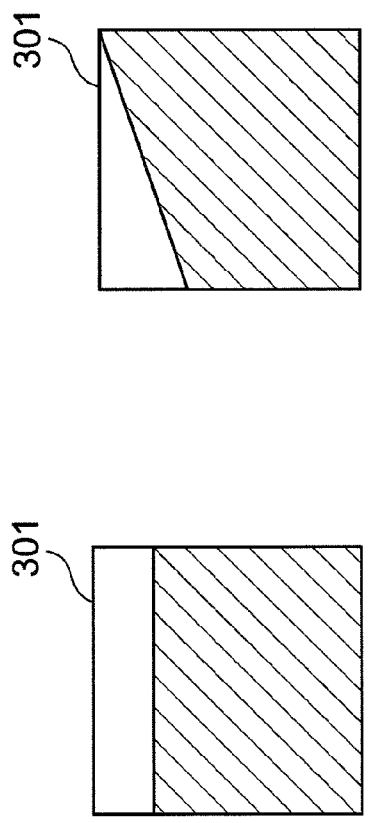
FIG. 4C is a schematic view showing a medical image when an acoustic coupler is mounted.
Figure 4D:
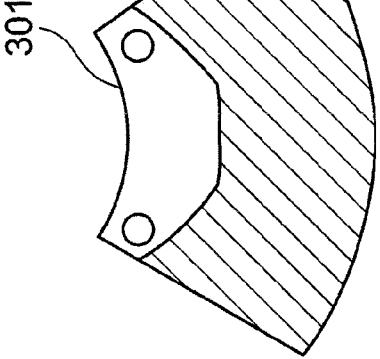
FIG. 4D is a schematic view showing a medical image when an acoustic coupler is mounted.

For example, the acoustic coupler 300 to be used may be such that: the cross-sectional shape of the front surface is flat as shown by the coupler region 301 of FIG. 4A; the cross-sectional shape of the front surface linearly tilts from one side surface to the other side surface as shown by the coupler region 301 of FIG. 4B; the radius of curvature of the front surface is greatly gentler than that of the rear surface, that is, greatly gentler than that of the ultrasound transmission/reception surface as shown by the coupler region 301 of FIG. 4C; or the radius of curvature of the front surface is greatly steeper than that of the rear surface, that is, greatly steeper than that of the ultrasound transmission/reception surface as shown by the coupler region 301 of FIG. 4D. It depends on a diagnosed site and so on whether the acoustic coupler 300 is to be mounted and what type of acoustic coupler is to be mounted.

The acoustic coupler 300 shown in FIG. 4C is used in such a case that, when a convex probe is used, ensuring a wide angle of view is desired but pressing the ultrasound transmission/reception surface strongly against a living body makes the patient feel pain or places load on the ultrasound probe 101 to adversely affect durability. The acoustic coupler 300 shown in FIG. 4D is used, for example, for making it easier to apply between ribs.

Figure 4E:
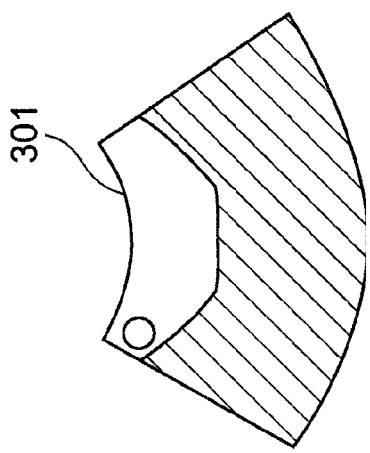
FIG. 4E is a schematic view showing a medical image when an acoustic coupler is mounted.
Figure 4F:
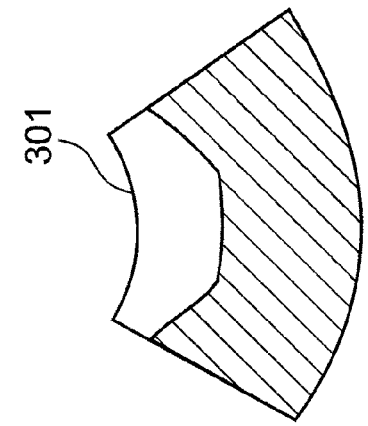
FIG. 4F is a schematic view showing a medical image when an acoustic coupler is mounted.
Figure 5A:
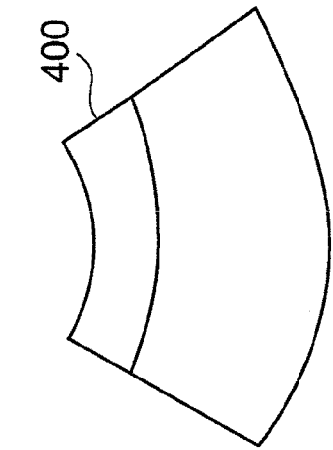
FIG. 5A is a schematic view showing a pattern resembling a shape of an acoustic coupler.
Figure 5B:
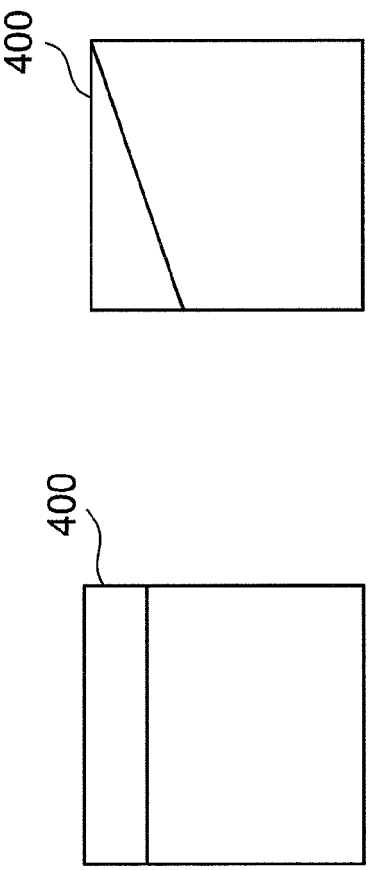
FIG. 5B is a schematic view showing a pattern resembling a shape of an acoustic coupler.
Figure 5C:
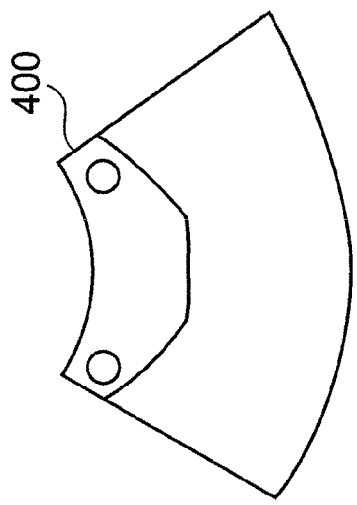
FIG. 5C is a schematic view showing a pattern resembling a shape of an acoustic coupler.
Figure 5D:
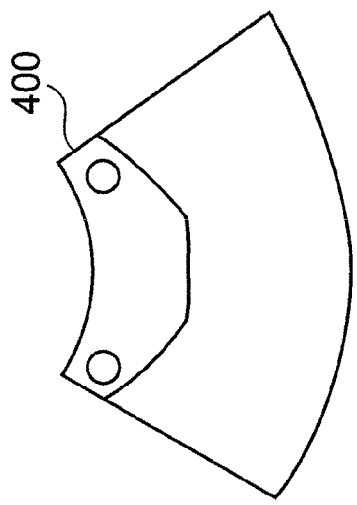
FIG. 5D is a schematic view showing a pattern resembling a shape of an acoustic coupler.
Figure 5E:
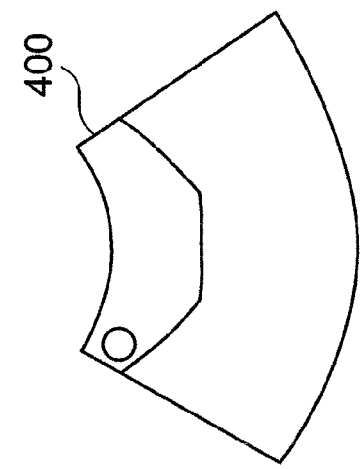
FIG. 5E is a schematic view showing a pattern resembling a shape of an acoustic coupler.
Figure 5F:
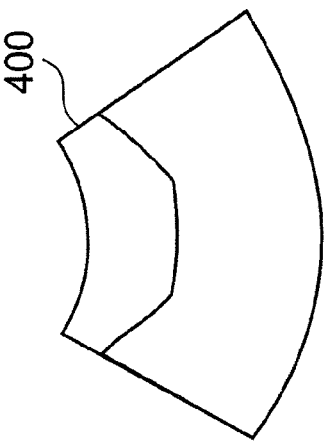
FIG. 5F is a schematic view showing a pattern resembling a shape of an acoustic coupler.

Further, as shown by the coupler regions 301 of FIGS. 4E and 4F, the acoustic coupler 300 may be provided with an implanted identifier such as a metal pipe having different acoustic impedance from that of the material for coupler. The metal pipe can be recognized on a medical image because the acoustic impedance thereof is different from that of the material for coupler. In order that the type of the acoustic coupler 300 can be specified, the cross-sectional shape and implanted position of the metal pipe vary with the type. For example, the acoustic coupler 300 shown in FIG. 4E is different in cross-sectional shape from the acoustic couplers 300 shown in FIGS. 4A-4D in that the metal pipe is implanted near a side surface. Thus, the type is identified based on the difference in cross-sectional shape. Moreover, the acoustic coupler 300 shown in FIG. 4F is different in cross-sectional shape from the acoustic coupler 300 shown in FIG. 4E in that the metal pipes are implanted near both side surfaces. Thus, the types of the both are identified based on the difference in cross-sectional shape.

With reference to FIG. 1 again, a signal voltage applied to the ultrasound probe 101 is supplied from the transceiver 102. The transceiver 102 has a transmitter and a receiver. Both the transmitter and the receiver are connected to the electrode pairs. The transmitter applies a predetermined signal voltage to the respective electrode pairs.

The receiver receives echo signals transmitted from the respective electrode pairs.

Into the transmitter and the receiver, control parameters such as a transmission voltage, a transmission waveform, a pulse repetition frequency, an ultrasound scan range, a focus, a gain, and a sound speed value are inputted by the controller 106. Then, in accordance with the control parameters, the signal voltage is applied and the echo signals are received.

The transmitter generates a pulse signal of a frequency corresponding to the pulse repetition frequency of the control parameters. The transmitter delays the pulse signal for each of the ultrasound transducers 212 in accordance with the ultrasound scan range and the focus of the control parameters. Then, the transmitter converts the signal into a high voltage corresponding to the transmission voltage of the control parameters and applies the voltage to the ultrasound transducers 212.

The receiver amplifies the received echo signals in accordance with the gain of the control parameters. Then, the receiver converts the amplified echo signals into digital signals. Further, the receiver gives a delay time necessary for determining the reception directionality to the digital signals obtained by conversion, by a signal delay amount corresponding to the sound speed value of the control parameters, and performs phasing and addition. Through the phasing and addition, such a single echo signal is generated that a reflection component from a direction corresponding to the reception directionality is enhanced.

The echo signal is outputted from the receiver to the signal processor 103. The signal processor 103 executes signal processing for medical image generation on the echo signal, thereby obtaining raster image data. In the signal processing for medical image generation, a band-pass filter process is executed on the echo signal. After that, an envelope curve is detected. Then, a compression process by logarithmic transformation is executed on the detected data to obtain the raster image data of a medical image.

The raster image data is inputted from the signal processor 103 into the image processor 105 through an image memory. The image processor 105 converts the raster image data into a video format of orthogonal coordinate system by a scan conversion process. The image data converted into the video format is outputted to the monitor 104.

The monitor 104 displays the image data of a medical image.

The analyzer 107 analyzes a generated medical image. Based on the analysis, the analyzer 107 identifies presence/absence of mounting of the acoustic coupler 300 and the type of the mounted acoustic coupler 300. The controller 106 outputs the control parameters corresponding to the result of the analysis by the analyzer 107, thereby controlling the transceiver 102.

The analyzer 107 stores patterns 400 that resemble the various cross-sectional shapes of the acoustic couplers 300. The patterns 400 may be object data like figures, or may be numerical data indicating the magnitude relation of numerical values between the respective positions of the cross-sectional shapes and other positions.

FIGS. 5A, 5B, 5C, 5D, 5E and 5F are diagrams schematically showing the patterns 400 stored by the analyzer 107. The pattern 400 shown in FIG. 5A resembles the cross-sectional shape of the acoustic coupler 300 shown in FIG. 4A, and the lower surface of the pattern 400 is flat as the front surface of the acoustic coupler 300 is. The pattern 400 shown in FIG. 5B resembles the cross-sectional shape of the acoustic coupler 300 shown in FIG. 4B, and the lower surface of the pattern 400 linearly slopes from one side surface to the other side surface. The pattern 400 shown in FIG. 5C resembles the cross-sectional shape of the acoustic coupler 300 shown in FIG. 4C, and the radius of curvature of the lower surface of the pattern 400 is the same as that of the front surface of the acoustic coupler 300. The pattern 400 shown in FIG. 5D resembles the cross-sectional shape of the acoustic coupler 300 shown in FIG. 4D, and the radius of curvature of the lower surface of the pattern 400 is the same as that of the front surface of the acoustic coupler 300. The pattern 400 shown in FIG. 5E resembles the cross-sectional shape of the acoustic coupler 300 shown in FIG. 4E, and the cross-section of the metal pipe is shown close to one side surface. The pattern 400 shown in FIG. 5F resembles the cross-sectional shape of the acoustic coupler 300 shown in FIG. 4F, and the cross-sections of the metal pipes are shown close to both the side surfaces.

The analyzer 107 determines whether the coupler region 301 representing the acoustic coupler 300 exists on a medical image. When the coupler region 301 exists, the analyzer 107 puts the coupler region 301 into the respective patterns 400 and selects the pattern 400 that matches the coupler region 301. Existence of the coupler region 301 is determined based on whether a region in which pixel values representing the acoustic coupler 300 gather exists in the upper part of the medical image.

The controller 106 previously stores combinations of the control parameters. The respective combinations of the control parameters are in one-to-one association with the results of the analysis of the analyzer 107. The controller 106 reads out one of the combinations of the control parameters based on the result of the analysis by the analyzer 107 and outputs the combination to the transceiver 102. With output of the control parameters, the ultrasound diagnosis apparatus 100 transmits and receives ultrasound waves in accordance with presence/absence of mounting of the acoustic coupler and the type of the acoustic coupler 300 when the acoustic coupler 300 is mounted, and generates a medical image.

The analyzer 107 and the controller 106 determine whether the acoustic coupler 300 is mounted and, in a case that the acoustic coupler 300 is mounted, identify the type of the acoustic coupler 300.

Further, the analyzer 107 and the controller 106 determine the ultrasound transmission/reception conditions corresponding to identification of the acoustic coupler 300 at predetermined intervals, for example, every 10 seconds (this interval can be arbitrarily set).

That is to say, the identification and the determination of the ultrasound transmission/reception conditions are automatically executed. The ultrasound diagnosis apparatus 100 may have, for example, a button on the ultrasound probe 101 so that the identification and the determination of the conditions are executed when the button is pressed down.

Figure 6:
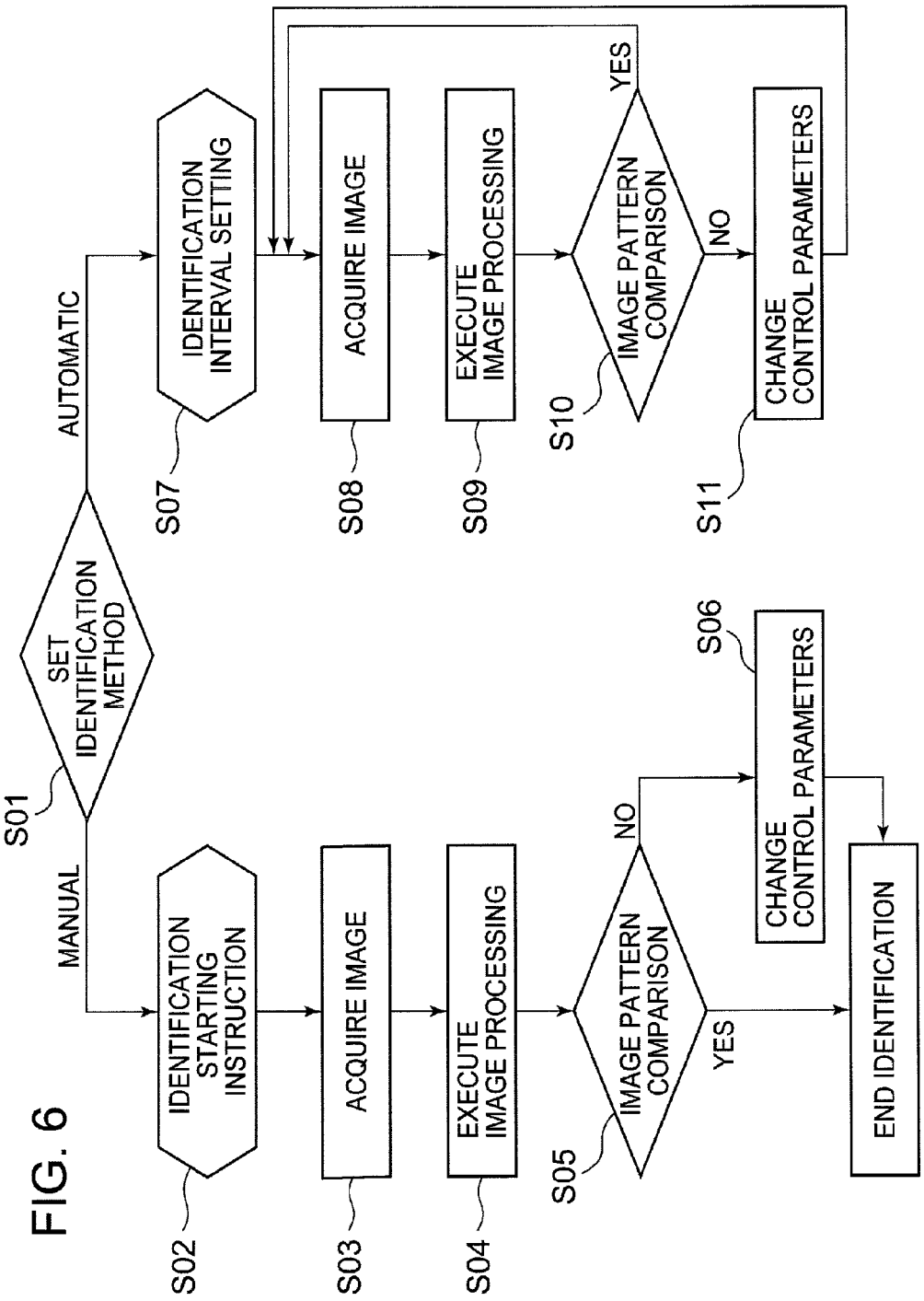
FIG. 6 is a flow chart showing an operation for identifying an acoustic coupler.

FIG. 6 is a flow chart showing an operation by the controller 106 for determining whether the acoustic coupler 300 is mounted and identifying the type of the acoustic coupler 300 when the acoustic coupler 300 is mounted.

The controller 106 sets a method for identifying the coupler region 301 and the pattern 400, whether manually or automatically (S01). In the case of manual identification, identification is started based on an identification starting instruction inputted into the controller 106 (S02).

The image processor 105 acquires a medical image (S03). The image processor 105 executes image processing on the acquired medical image so as to form the pattern 400 (S04).

The analyzer 107 executes image pattern comparison between the coupler region 301 and the pattern 400 and, in a case that the coupler region 301 and the pattern 400 match each other (S05, YES), the controller 106 outputs control parameters corresponding to the pattern 400 matching the coupler region 301, to the transceiver 102, and ends the identification.

On the other hand, in a case that the coupler region 301 and the pattern 400 do not match each other (S05, NO), the controller 106 changes to control parameters for a case that the acoustic coupler 300 is not mounted (S06), outputs the control parameters to the transceiver 102, and ends the identification.

In the case of automatic identification of the coupler region 301 and the pattern 400, the controller 106 sets an identification interval inputted therein (S07).

The image processor 105 acquires a medical image (S08). The image processor 105 executes image processing on the acquired medical image so as to form the pattern 400 (S09).

The analyzer 107 executes image pattern comparison between the coupler region 301 and the pattern 400 and, in a case that the coupler region 301 and the pattern 400 match each other (S10, YES), the controller 106 outputs control parameters corresponding to the pattern 400 matching the coupler region 301, to the transceiver 102, and continues the image pattern comparison.

On the other hand, in a case that the coupler region 301 and the pattern 400 do not match each other (S10, NO), the controller 106 changes to control parameters for a case that the acoustic coupler 300 is not mounted (S11), outputs the control parameters to the transceiver 102, and continues the image pattern comparison.

A specific example of the ultrasound diagnosis apparatus 100 will be described.

In a case that the acoustic coupler 300 appropriate for transmitting and receiving ultrasound waves to and from between ribs as shown in FIG. 4D is mounted, the medical image shown in FIG. 4D is outputted from the image processor 105. Since the coupler region 301 exists in the upper part of the medical image, the analyzer 107 puts each of the patterns 400 into the medical image to select the pattern 400 shown in FIG. 5D. Then, the controller 106 outputs, to the transceiver 102, the control parameters corresponding to the selected pattern 400. Consequently, after the control parameters are outputted, as shown in FIG. 7, the ultrasound scan range is narrowed more than the contact surface 500, namely, the front surface of the acoustic coupler 300, and ultrasound waves are transmitted and received. The control parameters with the ultrasound scan range 510, 520 narrowed are such that a frame rate is increased by eliminating an unnecessary scan range because the ribs do not transmit ultrasound waves.

Thus, the ultrasound diagnosis apparatus 100, based on the presence/absence and shape of a coupler region shown in a medical image, identifies presence/absence of mounting of an acoustic coupler and the type of the acoustic coupler when the acoustic coupler is mounted. Therefore, it becomes possible to identify an acoustic coupler without providing an ultrasound probe and the acoustic coupler with special structures. Moreover, it becomes possible to appropriately regulate the control parameters in accordance with the type of the identified acoustic coupler, and therefore, it becomes possible to increase the amount of information of an image to be obtained and increase a diagnosis capability.

What is claimed is:

1. An ultrasound diagnosis apparatus, comprising:
   an ultrasound probe provided with an ultrasound transmission/reception surface and an acoustic coupler, the acoustic coupler being provided with the ultrasound probe so as to cover the ultrasound transmission/reception surface;
   a generator configured to, based on the ultrasound waves received by the ultrasound probe, generate an image expanding in a depth direction from the ultrasound transmission/reception surface;
   an analyzer configured to identify a type of the acoustic coupler, based on a cross-sectional shape of an acoustic coupler within the image generated by the generator; and
   a controller configured to control ultrasound transmission/reception conditions of the ultrasound probe,
   wherein the controller is further configured to change the ultrasound transmission/reception conditions based on the type of the acoustic coupler identified by the analyzer.

2. The ultrasound diagnosis apparatus according to claim 1, wherein the analyzer is further configured to store patterns representing various cross-sectional shapes of the acoustic coupler within the image in accordance with the type of the acoustic coupler and identify the type of the acoustic coupler by matching the patterns with the image generated by the generator.

3. The ultrasound diagnosis apparatus according to claim 1, wherein the controller is configured to, when the type of mounting of the acoustic coupler is the acoustic coupler having the ultrasound transmission/reception surface with a larger radius of curvature than a radius of curvature of the ultrasound transmission/reception surface of the ultrasound probe identified by the analyzer, restricts a range to scan with the ultrasound waves to a range that is narrower than the ultrasound transmission/reception surface of the acoustic coupler.

4. The ultrasound diagnosis apparatus according to claim 1, wherein the analyzer is further configured to perform the identification at predetermined time intervals.

* * * * *